(12) United States Patent
Hehrlein (10) Patent No.: US 10,420,581 B2
(45) Date of Patent: Sep. 24, 2019

(54) DEVICE FOR DETACHING PARIETAL THROMBI FROM A BLOOD VESSEL

(71) Applicant: UNIVERSITAETSKLINIKUM FREIBURG, Freiburg (DE)

(72) Inventor: Christoph Hehrlein, Freiburg (DE)

(73) Assignee: UNIVERSITATSKLINIKUM FREIBURG, Freiburg (DE)

( * ) Notice: Subject to any disclaimer, the term of this patent is extended or adjusted under 35 U.S.C. 154(b) by 326 days.

(21) Appl. No.: 14/361,710

(22) PCT Filed: Nov. 12, 2012

(86) PCT No.: PCT/EP2012/004694
§ 371 (c)(1),
(2) Date: May 30, 2014

(87) PCT Pub. No.: WO2013/079156
PCT Pub. Date: Jun. 6, 2013

(65) Prior Publication Data
US 2015/0088174 A1 Mar. 26, 2015

(30) Foreign Application Priority Data
Nov. 30, 2011 (DE) .................. 10 2011 120 004

(51) Int. Cl.
*A61B 17/3207* (2006.01)
*A61M 25/01* (2006.01)
(Continued)

(52) U.S. Cl.
CPC .............. *A61B 17/320725* (2013.01); *A61B 17/320783* (2013.01); *A61M 25/0043* (2013.01);
(Continued)

(58) Field of Classification Search
CPC ............ A61B 17/320725; A61B 17/22; A61B 17/221; A61B 17/22031; A61B 17/3207;
(Continued)

(56) References Cited

U.S. PATENT DOCUMENTS 5,273,527 A 12/1993 Schatz et al.
5,549,556 A * 8/1996 Ndondo-Lay ....... A61M 25/104
604/103.1
(Continued)

FOREIGN PATENT DOCUMENTS

DE 693 13 510 T2 3/1998
DE 101 25 998 A1 11/2002
(Continued)

*Primary Examiner* — Katrina M Stransky
*Assistant Examiner* — Lindsey Bachman
(74) *Attorney, Agent, or Firm* — Fitch, Even, Tabin & Flannery LLP (57) ABSTRACT

A device for detaching parietal thrombi from a blood vessel is disclosed, comprising a catheter including at least one catheter section, wherein an outer diameter of the at least one catheter section is changeable and at least one wall opening extends transversely through a wall of the at least one catheter section. The catheter wall along the at least one catheter section is a resilient and deformable material. The catheter is transformed from a smaller catheter outer diameter to a uniform larger catheter outer diameter by a resilient change in shape. A displacement body can be introduced into the at least one catheter section which is transformed in diameter to deform the catheter from the smaller catheter outer diameter to the larger outer diameter for capturing thrombus material.

24 Claims, 3 Drawing Sheets

(51) Int. Cl.
*A61M 25/00* (2006.01)
*A61B 17/221* (2006.01)
*A61B 17/22* (2006.01)
*A61B 17/00* (2006.01)

(52) U.S. Cl.
CPC ....... *A61M 25/0102* (2013.01); *A61B 17/221* (2013.01); *A61B 2017/00942* (2013.01); *A61B 2017/22061* (2013.01); *A61B 2017/22079* (2013.01); *A61M 2025/0024* (2013.01); *A61M 2025/0063* (2013.01)

(58) Field of Classification Search
CPC .... A61B 17/320758; A61B 17/320783; A61B 2017/320741; A61M 2025/0024; A61M 2025/0063; A61M 25/0102
USPC ................................................ 606/108, 159
See application file for complete search history.

(56) References Cited

U.S. PATENT DOCUMENTS

| | | |
|---|---|---|
| 7,063,671 B2 | 6/2006 | Couvillon, Jr. |
| 7,618,434 B2 * | 11/2009 | Santra ................... A61B 17/221 606/200 |
| 2001/0051810 A1 * | 12/2001 | Dubrul ................. A61B 17/221 606/159 |
| 2005/0021071 A1 | 1/2005 | Konstantino et al. |
| 2005/0283166 A1 | 12/2005 | Greenhalgh |
| 2006/0064073 A1 | 3/2006 | Schonholz et al. |
| 2006/0074441 A1 | 4/2006 | McCuckin, Jr. et al. |
| 2006/0235458 A1 * | 10/2006 | Belson .............. A61M 25/0032 606/191 |
| 2006/0253145 A1 | 11/2006 | Lucas |
| 2007/0208361 A1 | 9/2007 | Okushi et al. |
| 2008/0300532 A1 | 12/2008 | Bonnette et al. |
| 2009/0270800 A1 | 10/2009 | Spurchise et al. |
| 2010/0030256 A1 * | 2/2010 | Dubrul ............... A61B 10/0266 606/200 |
| 2010/0087844 A1 | 4/2010 | Fischer, Jr. |
| 2010/0125239 A1 | 5/2010 | Perry et al. |
| 2010/0132748 A1 | 6/2010 | Kessler et al. |
| 2011/0040314 A1 | 2/2011 | McGuckin, Jr. et al. |
| 2013/0066348 A1 | 3/2013 | Fiorella et al. |
| 2013/0131703 A1 | 5/2013 | Fiorella et al. |
| 2013/0165871 A1 | 6/2013 | Fiorella et al. |

FOREIGN PATENT DOCUMENTS

| | | |
|---|---|---|
| DE | 20 2009 012 085 U1 | 1/2010 |
| DE | 10 2009 017 050 A1 | 4/2010 |
| EP | 0 385 920 A2 | 9/1990 |
| WO | WO 2007/089897 A2 | 8/2007 |
| WO | WO 2010/115642 A1 | 10/2010 |

\* cited by examiner

DEVICE FOR DETACHING PARIETAL THROMBI FROM A BLOOD VESSEL

CROSS REFERENCE TO RELATED APPLICATION

Reference is made to EP Patent Application Serial No. 10 2011 120 004.9, filed Nov. 30, 2011, which application is incorporated herein by reference in its entirety.

BACKGROUND OF THE INVENTION

Field of the Invention

The invention relates to a device for detaching parietal thrombi from a blood vessel, having a catheter along the catheter longitudinal extent including at least one catheter section, wherein an attributable catheter outer diameter of the at least one catheter section can be changed and, in an attributable catheter wall of the catheter section, at least one wall opening is introduced, which completely passes through the catheter wall, transversely with respect to the catheter longitudinal extent.

Description of the Prior Art

For the interventional therapy of vessels which are constricted by parietal thrombi through which flows bodily fluids, a plurality of catheter-based medical instruments are known, which provide a mild ablation of deposits on the vessel inner walls caused by aging or disease. These medical instruments, frequently also designated as thrombectomy catheter systems, have a catheter tip suitable for tissue ablation, through which ablated thrombus material is disposed of extracorporeally, which is mostly assisted by an underpressure prevailing within the catheter lumen.

For this purpose, a mechanical thrombectomy catheter system is disclosed in US Published Application 2010/0087844 A1, having a multi-lumen catheter, which is able to be positioned by a guiding and positioning wire relative to a thrombosis, which is initially pre-treated with a lysis solution via a flushing duct. Via an instrument duct running along the catheter, subsequently a scraping instrument constructed in the form of a basket emerges on the distal side out from the catheter and fragments the surrounding thrombus material are removed by an axial back and forth movement. The separated thrombus material fragments can be collected via a further aspiration duct provided along the catheter, and can be delivered extracorporeally.

In contrast to the axially movable scraping instrument embodied in the manner of a basket, as explained above, US Published Applications 2006/0074441 A1 and 2011/0040314 A1 show thrombus material removal instruments constructed in wire form, which respectively have a sinusoidal wire form constructed on an instrument tip, which on rotation about the wire longitudinal axis assumes the effect of a spindle-shaped cutting structure. Upon coming into contact with thrombus material which adheres to the vessel wall, the instrument tip is able to break up the thrombus material from the rotatory shearing forces of the tip, and remove them. Detached thrombus material fragments are also delivered extracorporeally here by a suitably placed aspiration catheter.

A further thrombus material ablating instrument is described in US Published Patent Application 2006/0064073 A1, which discloses an instrument catheter guided through an aspiration catheter. At the distal catheter region of the instrument catheter, an ablation means which is wedge shaped rotates radially relative to the catheter axis for separating and fragmenting intravascular thrombus material by the rotation about the catheter axis. Through the tool arm which is wedge shaped, and the suction effect prevailing from the aspiration catheter, the fragmented thrombosis material particles move in proximal direction from the instrument catheter tip into the aspiration catheter. An advantageous addition to the mechanical thrombectomy catheter system described above is described in US Published Patent Application 2006/0253145 A1, in which at the distal end of the instrument catheter an inflatable balloon is located, which on the one hand centers the instrument catheter axially within the vessel and therefore relative to the thrombus material which is to be removed. On the other hand, fragments of thrombus material which are separated from the vessel wall cannot enter in an uncontrolled manner into the bloodstream on the distal side of the rotating fan-shaped instrument.

US Published Patent Application 2007/0208361 A1 describes an atherectomy catheter system which provides an aspiration catheter which is overlapped on the distal side by a radially expandable stent mesh and a centrally guided needle, which are mounted in a jointly co-rotating manner, and punctures, separates and breaks up thrombus material by advancing on the distal side along a stenotic blood vessel in a comparable manner to a drill head. The fragmented thrombus material pieces are delivered extracorporeally via the aspiration catheter.

Catheter systems with cutting instruments present a further device for the local separation of stenoted tissue regions. US Published Patent Application 2009/0270800 A1 discloses a catheter having at a distal peripheral outer region at which expansion bodies are disposed in circumferential direction, to permit the individual axial position of the distal catheter tip relative to a vessel which is to be treated. Furthermore, within the catheter a cutting blade is provided, which is guided by the catheter tip, to provide thrombus material to be separated from the vessel wall. Separated thrombus material pieces then arrive via an aspiration duct along the catheter arrangement.

A comparable catheter arrangement is disclosed in WO 2010/132748 A1, which likewise provides a cutting instrument which is mounted to be guided both axially through a radially expandable catheter tip and also via an opening provided laterally along the catheter arrangement.

US Published Patent Application 2008/0300532 A1 discloses a thrombectomy catheter, through which flows fluid, which is positioned by a guiding wire along a stenotic vessel site, and along which a distal catheter section has at least two openings oriented transversely to the catheter longitudinal extent. One opening functions as a fluid outlet opening from which a fluid stream strikes transversely to the vessel longitudinal extent onto the thrombus material which is to be removed and detaches this locally from the vessel inner wall with the formation of minimal-sized thrombus material fragments. The detached thrombus fragments flow via the second opening into the interior of the catheter, along which the fluid flow, interspersed with thrombus material, flows extracorporeally toward the exterior.

Finally, DE Published Patent Application 10 2009 017 050 A1 describes a device for the detaching of concretions from a blood vessel with a catheter, through which an instrument catheter is to be positionable relative to a thrombosis which is to be removed. The instrument catheter has a catcher element constructed as a stent, which autonomously expands radially after extraction from the catheter on the distal side. The catcher element has inlet openings, constructed as longitudinal slots, through which the material which is to be removed, in particular thrombi, penetrates into the interior of the catcher element. The axial and rotatory movements of the instrument catheter provide shearing forces which detach the thrombus material, projecting through the inlet openings into the interior of the catcher element. The thrombus material can be delivered extracorporeally in the form of fragmented individual pieces by application of a vacuum applied within the instrument catheter. For the removal of the catheter arrangement from the vessel, the catcher element is drawn into the duct in proximal direction through radially acting compression forces, and in this compressed state is removed extracorporeally.

All the above known solutions represent catheter constructions which are in part technically complex, the operative handling of which presents high demands on the operator, especially since the mostly sharp-edged instruments for local intravascular removal of parietal thrombi are to be operated with great care, in order to avoid injuries to vessel walls.

US Published Patent Application 2010/0125239 A1 illustrates a catheter with an inflatable balloon, by which medicaments can be applied to a particular site within a lumen, for example, an artery. In a variant embodiment, the balloon is surrounded by a porous membrane. A medicament is situated in the intermediate space between balloon and membrane. By the activation of electrodes situated on the membrane, and the thermal energy which is supplied in so doing, the membrane pores open and molecules of a medicament are pressed by the pressure generated by the balloon through the membrane pores to the tissue which is to be treated. In addition, the balloon brings about a radial expansion, in which the catheter comes in contact with the surrounding tissue.

The devices disclosed in U.S. Pat. No. 7,063,671 B2 disclose the taking of samples or the removal of polyps from a body of a patient include actuators of electroactive polymer material, which can be contracted or expanded by electrical stimulation. By corresponding actuation of the actuators, openings in the device can be expanded, in order to surround a sample or the polyp.

SUMMARY OF THE INVENTION

The invention is based on development of a device for detaching parietal thrombi from a blood vessel in a manner which is as simple, favorably priced and as easily operated by the operator as possible, so that a vessel wall injury can be largely prevented. In addition, parietal thrombus material is to be removed safely and efficiently, which is as free of residue as possible, from the vessel wall, and the thrombus fragments separated from the vessel wall are to be safely delivered extracorporeally.

The device according to the invention differs from the closest prior art, which is described in the publication of German Patent Application DE 10 2009 017 050 A1 discussed above The invention is a device for detaching parietal thrombi from a blood vessel having a catheter extending longitudinally which includes at least one catheter section. In the at least one catheter section at least one wall opening is provided, which completely passes through the catheter wall transversely with respect to the longitudinal extension, and includes means for changing the outer diameter, of at least the catheter section.

The device according to the invention is characterized by the catheter wall having the at least one catheter section including a wall having at least one wall opening which is made from a resiliently deformable material, which preferably is a resiliently deformable elastomer, constructed in a pipe or tube shape and surrounds an inner catheter lumen. The catheter, is made from a resiliently deformable material, which can be transformed by a separate means from a smaller catheter outer diameter to a relatively larger uniform catheter outer diameter which change in diameter is a resilient change in shape. The means exerts an external constraint on the catheter and can have at least one wall opening. The means may be a displacement body which can be introduced into the at least one catheter section to uniformly change the outer diameter and the catheter. When the constraint acting on the catheter from the exterior is eliminated, preferably by separation of the means from the catheter or by elimination of the interaction between the means and the catheter, the catheter autonomously assumes a relaxed state of the relatively smaller catheter outer diameter due to resilient resetting forces inherent in the material from which the catheter is made.

The at least one wall opening preferably may be a slot, a round or an oval opening or a many-sided opening, which upon transforming the catheter from the state with the relatively smaller catheter outer diameter to expand to the state with the relatively larger catheter outer diameter by removal of the external constraint. In the reverse case, the catheter autonomously reduces in size.

The catheter device according to the invention provides a local, intravascular removal of parietal thrombi by use of the operating principle of resilient resetting forces, which prevail in a comparable manner to a constrained radially expanded tube which is made from a resilient elastomer material. If, in addition, a local wall opening is introduced in the tube wall, for example in the form of a cut, the opening widens with the radial expansion of the tube section. A displacement body which is able to be introduced into the tube serves, for example, to provide the expansion. If, on the other hand, the displacement body is removed from the tube section, the inherent resilient resetting forces within the tube material provide for an autonomous reduction from the uniform larger diameter to the state of the original form, including a reduction in size or re-closing of the expanded wall opening.

If, in the radially expanded state, soft material in the form of thrombus material is brought into the widened wall opening, the wall opening surrounds the thrombus material situated in the wall opening and clamps the surround thrombus material very securely as soon as the external force causing the radial expansion of the tube diameter is removed. In this way, it is possible to remove thrombus material adhering to the vessel wall in portions and to deliver it extracorporeally by a catheter arrangement constructed according to the invention.

A simplest embodiment of the catheter system according to the invention therefore is a catheter made from a flexible, resilient wall material, which in the catheter wall at least in the distal catheter region has at least one wall opening. The wall opening can be achieved in various forms. Thus, for example, by a mere wall cut or a wall opening, may be introduced into the catheter wall by way of a punching process or by a similar material removal technique. The wall opening can have any desired opening cross-sectional shape. Thus, for example, round shapes or shapes deviating from a round cross-sectional shape may be used, such as, for example, many-sided cross-sectional shapes. A mandrel is introduced along the inner lumen of the catheter which has an outer diameter which is selected to be greater than the catheter inner diameter in the force-free state, to cause the expansion of the catheter. By introducing such a mandrel into the catheter, the catheter is uniformly expanded radially. The mandrel is made from a material which is dimensionally stable transversely to the mandrel longitudinal axis, but is flexible in the mandrel longitudinal direction, in order to thus be able to guide the mandrel through along curved vessel courses.

In a simplest embodiment, the mandrel has a smooth surface, which has an expanded wall opening at an inner boundary surface defining a volume determined by the wall opening width and depth, into which the thrombus material adhering to the wall can penetrate, in order for the fragmented thrombus material to subsequently be extracted in portions in the manner explained above.

In a preferred alternative embodiment, the mandrel has concave recesses on its mandrel surface, which in the case where the mandrel is introduced in the catheter are arranged congruently to the wall openings within the catheter wall. The shape and size of the concave recesses correspond to the shape and size of the wall openings or are larger than the shape and size of the wall openings. The boundary surface constructed in a concave manner defines the receiving volume of each individual wall opening. On one side, as described above, the receiving volume increases in size considerably compared with the case described above.

The use of a mandrel which is constructed to be hollow is particularly advantageous. The mandrel now itself has wall openings passing through the walls thereof, which in the case of the hollow mandrel introduced into the catheter, are arranged congruently to the wall openings within the catheter wall. In this case, also, the shape and size of the mandrel wall openings correspond to the shape and size of the wall openings of the catheter or are constructed larger than wall openings. In the case of a hollow mandrel, it is particularly advantageous to apply underpressure along the mandrel, by which the separation and removal process of the thrombus material, to be ablated respectively in portions, can be simplified.

Alternatively to the use of a mandrel, for the purposes of uniform radial expansion of the catheter it is also possible to provide an inflatable balloon which is able to be guided in a deflated state through the catheter, and is inflated in the catheter region in which the wall openings are provided, whereby the catheter is expanded uniformly radially at least in this region.

In both cases, namely the use of a mandrel in all its embodiment possibilities or of an inflatable balloon, the uniform radial expansion of the catheter positioned in a suitable manner within a vessel obstructed by thrombus material brings about an increase to the contact pressure of the catheter outer side onto parietal thrombus material, causing the thrombus material to be pressed extensively into the expanded wall openings within the catheter wall. By removing the mandrel from the catheter interior or by deflation of the balloon within the catheter interior, the catheter contracts radially autonomously owing to the resilient resetting forces inherent in the material. The thrombus material is situated within the wall openings. Upon reduction in diameter, the thrombus material is tightly held in the openings and is adherent to the blood vessel walls. Removal of the catheter shears the portion of the thrombus held by the walls and the portion is removed upon withdrawal of the catheter held securely in the wall openings.

In a preferred embodiment, the separation process can be assisted by axial and/or radial relative movements of the catheter relative to the stenoted vessel site. The relative movements can either be carried out manually by the operator or assisted by a vibrator unit provided in a suitable manner on the proximal side on the catheter.

Moreover, a further advantageous embodiment provides the connection of an underpressure source at least along the catheter, so that the separation process of the wall-adherent thrombus material and a subsequent safe removal of the detached thrombus material through the catheter on the proximal side can be assisted.

The catheter system according to the invention does not require any cutting instruments which in the prior art possibly injured the healthy vessel wall. Cutting instruments are guided intravascularly separately from the catheter, in the prior art. The catheter system according to the invention enables a mild and totally injury-free thrombus material ablation from the vessel inner wall, especially since on reaching the healthy vessel inner wall by the catheter, the healthy vessel wall material lies parallel to the catheter outer wall and is not able to extend into the expanded wall openings. The catheter, offset with lateral wall openings, is therefore only able to remove thrombus tissue which projects over the wall surface.

In order to completely eliminate parietal thrombus material, in most cases there is a need for a positioning of the catheter to be carried out several times in succession relative to the thrombus material which is present intravascularly using the separation process described above. It is indeed possible to draw the catheter back in proximal direction after each individual tissue separation through a working catheter which is also introduced intracorporeally, and to clean it accordingly extracorporeally of the separated tissue material, in order to position the catheter intracorporeally once again. However, in cases in which larger quantities of thrombus material are to be removed at a stenosis, it is advantageous to connect an underpressure source on the proximal side on the catheter, via which separated thrombus material within the catheter can be delivered extracorporeally on the proximal side.

Further advantageous embodiments can be seen from the further description with reference to the figures of the drawings.

BRIEF DESCRIPTION OF THE DRAWINGS

The invention is described below by way of example, without restriction of the invention, with the aid of example embodiments with reference to the drawings. There are shown.

DETAILED DESCRIPTION OF THE INVENTION

Figure 1A:
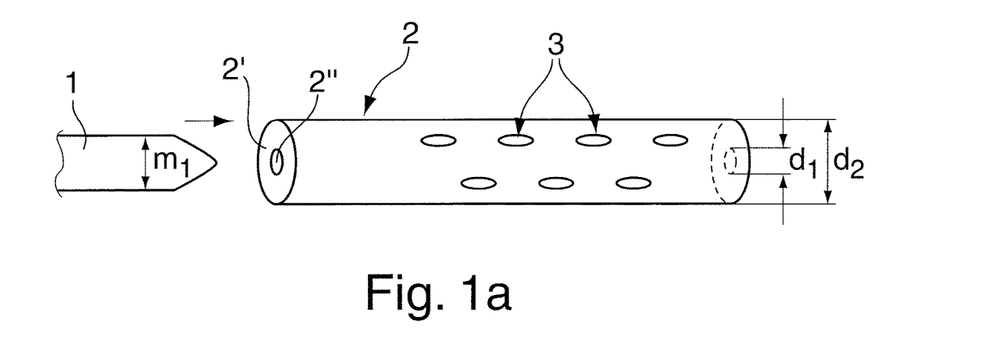
FIGS. 1a, b and c illustrate a catheter and mandrel in separated state (a) in joined state (b), and in a detailed view of an expanded wall opening in state (c)

FIG. 1a shows a longitudinal portion of the distal region of a catheter 2, which is constructed to be shaped as a pipe or tube which includes a catheter wall 2' of a resilient deformable elastomer material surrounding an inner catheter lumen 2". The elastomeric catheter wall material is preferably made from a material of the following materials:

Polymethyl methacrylate (PMMA), polytetrafluoroethylene (PTFE), polyurethanes, polyetherurethanes, silicone polyetherurethanes, silicone polyurethanes, silicone polycarbonate urethanes, polyolefin elastomers, polyisobutylenes, fluorosilicones, polyvinyl chloride (PVC), polydimethylsiloxane (PDMS), polyactides, polyethylene, polybutylmethacrylate, polyacrylamide, polyacrylonitriles, polyamides, polyetheramides, polyethylene amine polyimides, polycarbonates, polycarbourethanes, polyvinyl ketones, polyvinyl halogenides, polyvinylidene halogenides, polyvinyl ether, polyisobutylenes, polyvinyl aromates, polyvinyl ester, polyvinylpyrrolidones, polyoxymethylenes, polytetramethylene oxide, nylon or polyester.

In addition, wall openings 3 are introduced into the catheter wall with the number, arrangement, opening size and opening shape of the openings being configurable basically as desired. Preferably, in the state of the catheter shown in FIG. 1a, in which the catheter is free of any external applications of force, the wall openings 3 have a greater opening width in the longitudinal dimension than in the circumferential direction around the catheter 2. For example, the wall openings 3 can be embodied by local cuts in longitudinal direction within the catheter wall. It is not necessarily required to undertake to shape and size the wall openings 3 in a uniform manner. The wall openings 3 can have completely different sizes and shapes according to the arrangement pattern longitudinally and in circumferential direction with respect to the catheter.

In addition, in FIG. 1a, a mandrel 1 constructed in a shape of a rod is illustrated which is preferably made from a material which is constructed to be dimensionally stable transversely and flexible with respect to the mandrel longitudinal axis. For example, shaped bodies in a form of a rod or wire which is made of plastic or metal are suitable. The mandrel diameter $m_1$ is uniform and is greater than the inner diameter $d_1$ and preferably is greater than the catheter outer diameter $d_2$ of the catheter 2 illustrated in FIG. 1a.

Figure 1B:
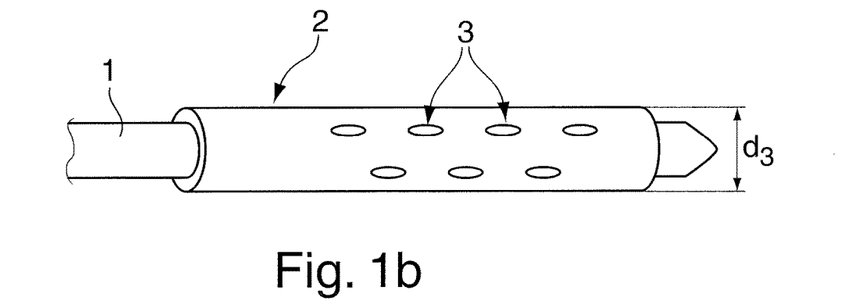
Figure 1C:
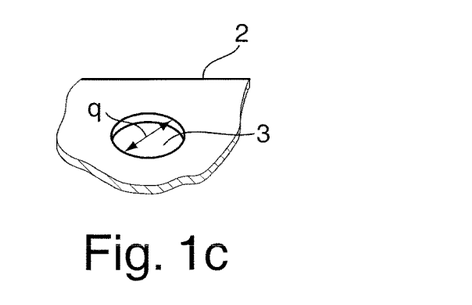

In FIG. 1b, a state is illustrated, during which the mandrel 1 is guided through the catheter to cause the mandrel 1 to uniformly radially expand the inner and outer diameter of catheter 2 made of a resilient material. In this state, the catheter 2 is expanded mechanically. Its diameter has an outer diameter $d_3$, which is greater than the catheter outer diameter $d_2$ according to FIG. 1a. Through the constrained radial expansion of the catheter 2 according to FIG. 1b, the wall openings 3 also undergo an opening expansion oriented at least in circumferential direction around the catheter 2, by way of the resilient deformation of the catheter wall 2'. In FIG. 1c a detailed view of an expanded wall opening 3 is shown within the radially opened catheter wall 2'.

Figure 6:
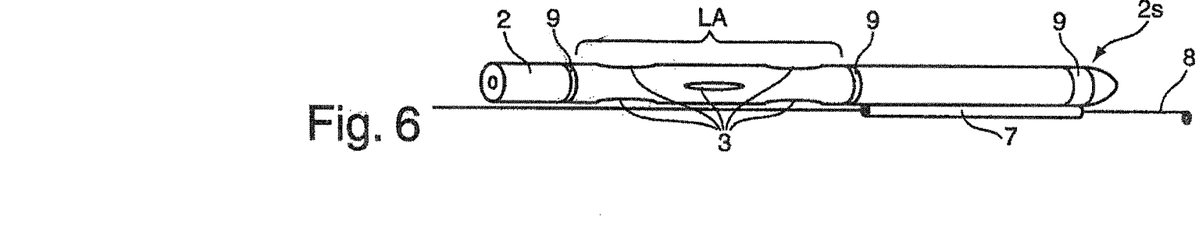
FIG. 6 illustrates a catheter utilizing guide lumen in the region of the catheter tip.

For the purposes of intravascular positioning in vessels, typically through which blood flows, the distal catheter section illustrated in FIG. 1a preferably ranges in length between 1 cm to 100 cm and the catheter outer diameter $d_2$ ranges between 0.5 mm and 25 mm depending on the medical application. The wall thickness w of the catheter 2 (FIG. 2(a)), which is free from external forces, typically measures between 0.1 mm and 2.5 mm.

It has proved to be particularly advantageous for the local removal of soft vessel thrombus material adhering to the wall to dimension the wall openings 3 so they have in the expanded state (see FIGS. 1b and 1c) a maximum opening width q of 0.1 mm to 15 mm.

As a result of the choice of resilient elastomeric material for the catheter wall 2', it is obvious that after removal of the mandrel 1 from the catheter 2, the catheter deforms back autonomously and immediately into the state with the smaller outer diameter $d_2$ resultant from the resilient resetting forces which are an inherent characteristic of the material, whereby at the same time the expanded wall openings 3 assume the original small wall opening geometry. The catheter system according to the invention utilizes the autonomous resetting process, which is based on the resilient resetting forces inherent in the material within the catheter, to achieve a mild removal of thrombus tissue within a blood vessel.

The mild tissue removal is illustrated diagrammatically in the following sequence images according to FIGS. 2a to 2c.

Figure 2A:
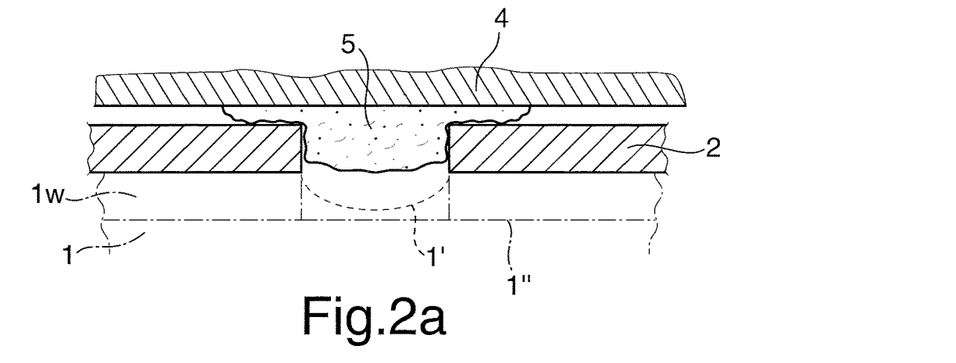
FIGS. 2a, b and c illustrate a sequence of image illustrations for the separation of vessel wall-adherent soft thrombosis material.

FIG. 2a shows a partial cross-section through a catheter 2 in the radially expanded state, positioned intravascularly relative to a thrombus 5 which adheres to a vessel wall 4, in which the mandrel 1 is introduced within the catheter 2. The wall opening 3 illustrated in cross-section in FIG. 2a is expanded which permits a portion of the vessel wall-adherent thrombus material 5 to project into the opening width of the wall opening 3. The uniform radial expansion of the catheter 2, in addition to the catheter outer wall 2 being pressed against the parietal thrombus material 5 of the vessel wall with a contact pressure which is predetermined by the selection of the geometry of the mandrel and catheter, causes the thrombus material to project into the wall opening 3 in the expanded wall.

Figure 2B:
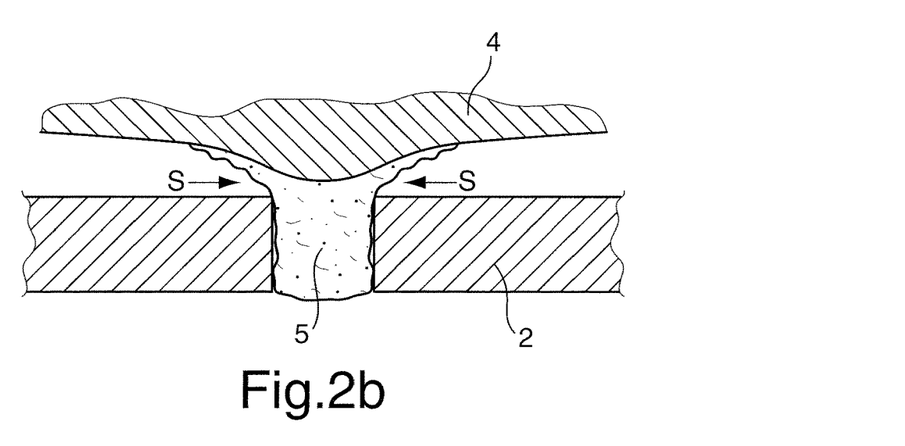

If in the next step the mandrel 1 is removed in a proximal direction from the catheter section, the resilient resetting forces described above come into action and bring about a contraction or a reduction in size of the wall opening 3, which causes the thrombus material 5 that is situated within the wall opening 3 to be thoroughly secured by the reduced size of the opening as shown in FIG. 2b.

Through the resilient deforming of the catheter 2 back to its original configuration, shearing forces S occur, which result in the thrombus material 5 being caught by the catheter 2, sheared off and separated from the residual material remaining on the vessel wall 4. FIG. 2c shows the state of the catheter 2 when the thrombus material 5 is separated from the vessel wall 4, which remains fixed securely along the catheter 2 within the constricted wall opening 3, in order to remove the separated thrombus material in the proximal direction.

Figure 2C:
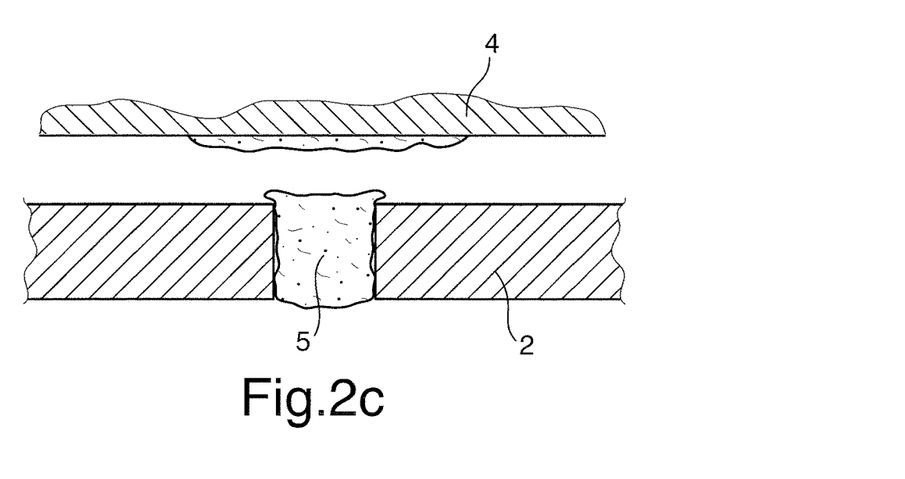

Advantageously, the separation process illustrated in FIGS. 2a to 2c can be additionally assisted by the application of an underpressure applied along the catheter 2.

A further advantageous alternative embodiment of the configuration of the mandrel 1 is illustrated in FIG. 2a. The surface contour 1', indicated in dashed lines, illustrates a local concave recess within the mandrel surface, which is arranged opposite the expanded wall opening 3 within the catheter 2. By such a recess 1', the tissue removal volume can be increased compared with a mandrel surface which is constructed to be flat.

In addition in FIG. 2a, a further alternative embodiment of the mandrel 1 has a hollow mandrel 1" which is indicated by the dot-and-dash lines 1"'. The hollow mandrel has at least one mandrel wall opening 1'" in the hollow mandrel wall 1w. The mandrel wall opening 1'", on the one hand causes the tissue removal volume to be further distinctly increased in size compared with the two alternatives described above, and on the other hand, it is possible to apply underpressure along the hollow mandrel to cause the thrombus material removal and separation to be significantly assisted.

Figures 3, 4:
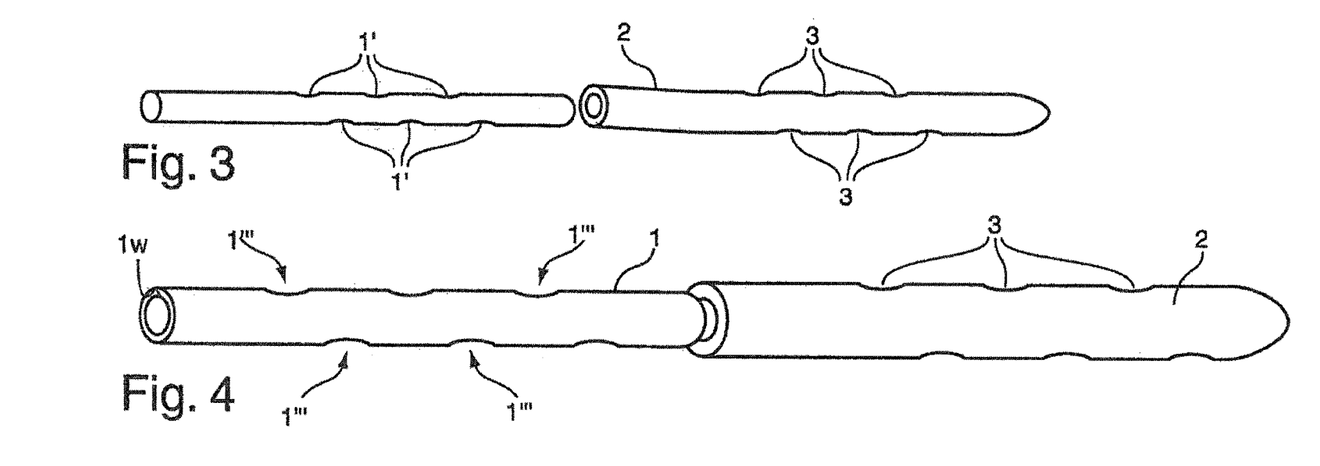
FIG. 3 illustrates an example embodiment of a mandrel with concave recesses.
FIG. 4 illustrates an example embodiment of a hollow mandrel with mandrel wall openings.

FIG. 3 shows a correspondingly manufactured mandrel 1 which has on the mandrel surface local concave recesses 1', which coincide or largely coincide in size and arrangement with the wall openings 3 introduced within the catheter 2 in the radially expanded state. The catheter 2 typically has a distal catheter tip 2s (FIG. 6).

FIG. 4 shows a hollow mandrel with mandrel wall openings 1''' in the mandrel wall 1w, which coincide or respectively largely coincide in size and arrangement with the wall openings 3 introduced within the catheter 2 in the radially expanded state.

Figure 5:
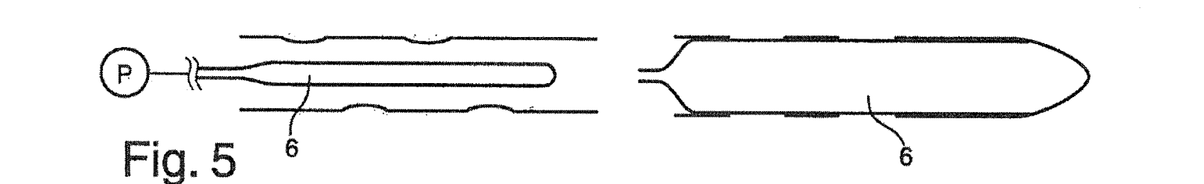
FIG. 5 illustrates a catheter system utilizing an inflatable balloon.

FIG. 5 shows an alternative embodiment with an inflatable balloon 6 which may be introduced axially along the catheter 2. The balloon 6 is connected in proximal direction with a pump device P. In the deflated state, the balloon 6 does not exert any forces which act radially onto the catheter 2 (see right-hand illustration in FIG. 5). If, on the other hand, the balloon 6 is inflated (see left-hand illustration, then the pneumatic forces exert a radially oriented resilient deformation which press against the catheter 2 causing the latter to assume the uniformly radially expanded state explained above. By corresponding deflation of the balloon 6, the catheter 2 assumes autonomously its original form again.

In FIG. 6 a portion LA of the catheter 2 is illustrated which is provided with the at least one wall opening 3. The longitudinal portion LA is spaced apart from the catheter tip 2s on the proximal side. For the intracorporeal positioning of the catheter 2 and, in particular, its longitudinal portion LA relative to parietal thrombus material on the vessel wall, the catheter 2 has an additional guide lumen 7 between the catheter longitudinal portion LA and the catheter tip 2s. The guide lumen 7 as illustrated is arranged on the outer wall of the catheter 2, through which a guide wire 8 is guided. Of course, the guide lumen 7 is preferably provided integrally within the catheter 2. The length of the guide lumen 7 typically measures between 20 to 50 mm.

In order for an operator to be able to monitor the positioning process of the catheter relative to a vessel region affected by thrombus material, radio-opaque markings 9 are arranged along the catheter 2, in particular on the catheter tip 2s and/or in the region of the catheter longitudinal portion LA which are visibly prominent on online X-ray images.

All the described catheter embodiments have catheter 2, closed with a catheter tip 2s. Of course, catheter tips 2s which are constructed to be open are also conceivable, in order in this way, for example, to remove by underpressure, thrombus material situated on the distal side immediately in front of the catheter tip 2s.

The catheter system described above is characterized by its simple component structure and guarantees a safe and mild removal of intravascular, soft tissue deposits. The catheter system according to the invention is applicable to all fields of intravascular vessel medicine, thus in particular for interventional radiology, angiology, cardiology or cardiac and vascular surgery.

LIST OF REFERENCE NUMBERS 1 mandrel
1' concave recesses
1'' dot-and-dash line, hollow mandrel
1''' mandrel wall opening
1w mandrel wall
2 catheter
2' catheter wall
2'' catheter lumen
3 wall opening
4 vessel wall
5 thrombus material
6 balloon
1' concave recess
d1 catheter inner diameter in force-free state
d2 catheter outer diameter in force-free state
d3 catheter outer uniform diameter in radially expanded state
m1 mandrel diameter
q wall opening diameter in expanded state
P pump device

The invention claimed is:

1. A device for detaching at least one parietal thrombus from a vessel wall comprising:
a resilient deformable catheter section including a wall and a plurality of openings passing completely through the wall, each opening comprising means for detaching at least one parietal thrombus which projects over the opening, the openings being separated longitudinally along the wall and being spaced apart around an outer circumference of the wall, an inner catheter lumen and the wall of the catheter section surrounding the inner catheter lumen and comprising a resilient deformable elastomer material and means for changing an inner and an outer diameter of the catheter section which is configured to be introduced longitudinally into the lumen for uniformly enlarging the inner and the outer diameter of the catheter section while the means for changing diameter is within the lumen and upon withdrawal of the means for changing diameter, the means for detaching contacts and captures at least part of the at least one parietal thrombus projecting at least over the opening and withdrawal of the means for changing diameter longitudinally along the catheter section from the lumen detaches and removes at least a captured part of the at least one parietal thrombus from the lumen.

2. The device according to claim 1, wherein:
the elastomer comprises at least one material of the following materials:
polymethyl methacrylate (PMMA), polytetrafluoroethylene (PTFE), polyurethanes, polyetherurethanes, silicone polyetherurethanes, silicone polyurethanes, silicone polycarbonate urethanes, polyolefin elastomers, polyisobutylenes, fluorosilicones, polyvinyl chloride (PVC), polydimethylsiloxane (PDMS), polyactides, polyethylene, polybutylmethacrylate, polyacrylamide, polyacrylonitriles, polyamides, polyetheramides, polyethylene amine polyimides, polycarbonates, polycarbourethanes, polyvinyl ketones, polyvinyl halogenides, polyvinylidene halogenides, polyvinyl ether, polyisobutylenes, polyvinyl aromates, polyvinyl ester, polyvinylpyrrolidones, polyoxymethylenes, polytetramethylene oxide, nylon or polyester.

3. The device according to claim 2, wherein:
the catheter section ranges from 1 cm to 100 cm in length, the catheter outer diameter ranges from 1 mm to 25 mm and a thickness of the catheter wall in a relaxed state ranges between 0.1 mm and 2.5 mm.

4. The device according to claim 3, wherein:
when the wall openings are in a state with the larger catheter outer diameter, a maximum width of the wall openings ranges from 0.1 mm to 15 mm.

5. The device according to claim 3, wherein:
the means for changing the inner and outer diameter comprises a mandrel which is flexible in a longitudinal direction and dimensionally stable transverse to the longitudinal direction, is dimensioned as a function of shape and size of the catheter section and upon introduction of the mandrel into the catheter, the inner and outer diameter to the catheter section is enlarged.

6. The device according to claim 5, wherein:
the mandrel includes at least one concave depression or recess located at a flat surface thereof and the at least one concave depression or recess is disposed relative to the surface of the mandrel so that when the mandrel is introduced into the catheter, the at least one concave depression or recess overlaps radially with the at least one opening.

7. The device according to claim 2, wherein:
when the wall openings are in a state with the larger catheter outer diameter, a maximum width of the wall openings ranges from 0.1 mm to 15 mm.

8. The device according to claim 2, wherein:
the means for changing the inner and outer diameter comprises a mandrel which is flexible in a longitudinal direction and dimensionally stable transverse to the longitudinal direction, is dimensioned as a function of shape and size of the catheter section and upon introduction of the mandrel into the catheter, the inner and outer diameter to the catheter section is enlarged.

9. The device according to claim 8, wherein:
the mandrel includes at least one concave depression or recess located at a flat surface thereof and the at least one concave depression or recess is disposed relative to the surface of the mandrel so that when the mandrel is introduced into the catheter, the at least one concave depression or recess overlaps radially with the at least one opening.

10. The device according to claim 1, wherein:
the catheter section ranges from 1 cm to 100 cm in length, the catheter outer diameter ranges from 1 mm to 25 mm and a thickness of the catheter wall in a relaxed state ranges between 0.1 mm and 2.5 mm.

11. The device according to claim 10, wherein:
when the wall openings are in a state with the larger catheter outer diameter, a maximum width of the wall openings ranges from 0.1 mm to 15 mm.

12. The device according to claim 10, wherein:
the means for changing the inner and outer diameter comprises a mandrel which is flexible in a longitudinal direction and dimensionally stable transverse to the longitudinal direction, is dimensioned as a function of shape and size of the catheter section and upon introduction of the mandrel into the catheter, the inner and outer diameter to the catheter section is enlarged.

13. The device according to claim 12, wherein:
the mandrel includes at least one concave depression or recess located at a flat surface thereof and the at least one concave depression or recess is disposed relative to the surface of the mandrel so that when the mandrel is introduced into the catheter, the at least one concave depression or recess overlaps radially with the at least one opening.

14. The device according to claim 1, wherein:
when the wall openings are in a state with the larger catheter outer diameter, a maximum width of the at least one opening ranges from 0.1 mm to 15 mm.

15. The device according to claim 1, wherein:
the wall openings are evenly distributed along the catheter section and also evenly distributed along a circumference of the catheter section.

16. The device according to claim 1, wherein:
the means for changing the inner and outer diameter comprises a mandrel which is flexible in a longitudinal direction and dimensionally stable transverse to the longitudinal direction, is dimensioned as a function of shape and size of the catheter section and upon introduction of the mandrel into the catheter, the inner and outer diameter to the catheter section is enlarged.

17. The device according to claim 16, wherein:
the mandrel includes at least one concave depression or recess located at a flat surface thereof and the at least one concave depression or recess is disposed relative to the surface of the mandrel so that when the mandrel is introduced into the catheter, the at least one concave depression or recess overlaps radially with the at least one opening.

18. The device according to claim 16, wherein:
the mandrel is hollow and includes a flat surface including at least one mandrel wall opening disposed along the flat surface of the mandrel such that when the hollow mandrel is introduced into the catheter section, at least one mandrel wall opening overlaps radially with at least one wall opening.

19. The device according to claim 1, wherein:
the means for changing comprises an inflatable balloon which is dimensioned as a function of shape and size of the catheter section so that when the balloon is introduced and inflated, the balloon transforms the section from a uniform smaller inner and outer diameter to larger uniform inner and outer diameter.

20. The device according to claim 1, wherein:
the catheter section includes a wall outer side which is hydrophilic.

21. The device according to claim 1, wherein:
on a proximal side the catheter section includes a connection for providing an under pressure or vibration.

22. The device according to claim 1, wherein:
at least one radio-opaque marking is disposed at least one of a tip of the catheter section and along the catheter section.

23. The device according to claim 1, comprising:
a lumen is located at a tip of the catheter section and ranges in length from 20-50 mm for guiding the catheter via a guide wire.

24. The device according to claim 1, wherein:
the wall openings are a slit, which are round or an oval, or a multiple-sided openings in cross-section which expand when the catheter section expands from the smaller catheter inner and outer diameter into the larger inner and outer diameter and reduces in size when the diameter of the catheter section contracts.

* * * * *